United States Patent [19]

Nagl et al.

[11] Patent Number: 5,274,184

[45] Date of Patent: Dec. 28, 1993

[54] ARYL SULPHIDE, ARYL SULPHOXIDE AND ARYL SULPHONE COMPOUNDS

[75] Inventors: Gert Nagl, Niederdorfelden; Hans-Tobias Macholdt, Darmstadt-Eberstadt, both of Fed. Rep. of Germany

[73] Assignee: Cassella Aktiengesellschaft, Frankfurt am Main, Fed. Rep. of Germany

[21] Appl. No.: 770,225

[22] Filed: Oct. 2, 1991

[30] Foreign Application Priority Data

Oct. 6, 1990 [DE] Fed. Rep. of Germany ....... 4031704
Mar. 21, 1991 [DE] Fed. Rep. of Germany ....... 4109261

[51] Int. Cl.$^5$ .................. C07C 317/14; C07C 323/62; C07D 213/55
[52] U.S. Cl. .................... 562/429; 546/267; 546/335; 546/342; 546/69; 560/9; 560/11; 560/12; 560/13; 560/17; 560/18; 562/432
[58] Field of Search .................. 562/432, 429; 556/69; 560/9, 11, 12, 13, 17, 18; 546/267, 335, 342

[56] References Cited

U.S. PATENT DOCUMENTS

| | | | |
|---|---|---|---|
| 1,769,423 | 7/1930 | Eder | 562/432 |
| 2,064,395 | 12/1936 | Tschunkur et al. | 562/432 X |
| 2,552,269 | 5/1951 | Emerson et al. | 562/432 X |
| 2,614,120 | 10/1952 | Caldwell | 560/91 |
| 4,480,021 | 10/1984 | Lu et al. | 430/106.6 |
| 4,493,802 | 1/1985 | Jaedicke et al. | 562/432 X |
| 4,686,303 | 8/1987 | Bauer et al. | 560/18 |
| 4,698,364 | 10/1987 | Janemura et al. | 514/563 |
| 4,902,826 | 2/1990 | Bauer et al. | 562/432 |

FOREIGN PATENT DOCUMENTS

CH-A-131255 4/1929 Switzerland.
CH-A-131289 4/1929 Switzerland.

OTHER PUBLICATIONS

Beilsteins Handbook, Der Organischen Chemie, Syst. No. 1068-1069, pp. 148-149, Berlin, (1927).

Primary Examiner—José G. Dees
Assistant Examiner—Vera C. Clarke
Attorney, Agent, or Firm—Connolly & Hutz

[57] ABSTRACT

The present invention relates to compounds of the general formula I

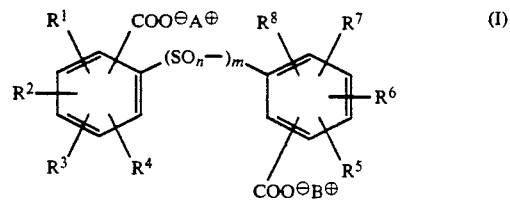

wherein $A^\oplus$ and $B^\oplus$ independently of one another denote a proton, with the limitation that they do not both simultaneously denote protons, the equivalent part of the barium ion, an ion of the general formula II

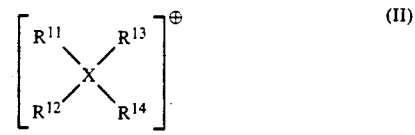

or an ion of the general formula III

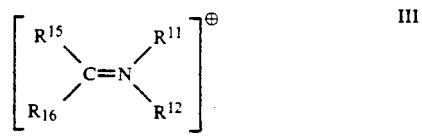

and wherein $R^1$ to $R^8$, $R^{11}$ to $R^{16}$, X and m and n are as defined in the description, processes for their preparation and their use as charge control agents in toners and developers and as charge improving agents in powders and varnishes.

7 Claims, No Drawings

ARYL SULPHIDE, ARYL SULPHOXIDE AND ARYL SULPHONE COMPOUNDS

The present invention relates to new aryl sulphide, aryl sulphoxide and aryl sulphone compounds and processes for their preparation.

The present invention relates to compounds of the general formula I

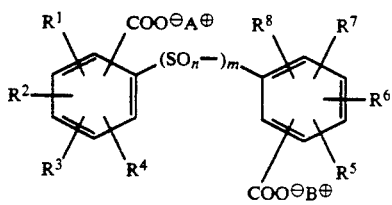

wherein n denotes 0, 1 or 2 if m denotes 1, and n denotes 0 if m denotes 2 or 3, $A^\oplus$ and $B^\oplus$ independently of one another denote a proton, with the limitation that they do not both simultaneously denote protons, or the equivalent proton of the barium ion, an ion of the general formula II

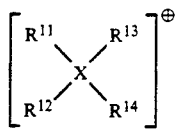

or an ion of the general formula III

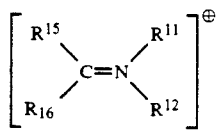

wherein X represents nitrogen, phosphorus, arsenic or antimony; $R^{11}$, $R^{12}$, $R^{13}$ and $R^{14}$ independently of one another represent hydrogen, with the limitation that they do not all simultaneously represent hydrogen; $(C_1-C_{30})$-alkyl; oxyethyl of the general formula —$(CH_2-CH_2-O)_p-R^9$, wherein $R^9$ is hydrogen, $(C_1-C_4)$-alkyl or acyl and p is a number from 1 to 10; $(C_5-C_{12})$-cycloalkyl; $(C_6-C_{12})$-aryl or $(C_8-C_{12})$-aryl-$(C_1-C_6)$-alkyl, it being possible for the radicals mentioned to be substituted by hydroxyl, $(C_1-C_4)$-alkoxy, primary, secondary or tertiary amino groups, acid amide groups, fluorine, chlorine or bromine; $R^{15}$ and $R^{16}$ independently of one another represent hydrogen, $(C_1-C_6)$-alkyl or amino of the general formula IV

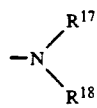

wherein $R^{17}$ and $R^{18}$ independently of one another denote hydrogen or $(C_1-C_8)$-alkyl; and it being possible for the radicals $R^{11}$ and $R^{13}$ or $R^{11}$ and $R^{15}$ independently of one another to form together a 5- to 12-membered ring system which is optionally substituted and/or contains further hetero atoms; $R^1$ to $R^8$ independently of one another denote hydrogen, $(C_1-C_{30})$-alkyl; $(C_2-C_{30})$-alkynyl; $(C_1-C_4)$-alkoxy; a group of the general formula —$((C_2-C_2)$-alkylene-O$)_q$-$R^{10}$, wherein $R^{10}$ is hydrogen, $(C_1-C_4)$-alkyl or acyl and q is a number from 1 to 10; $(C_5-C_{12})$-cycloalkyl; $(C_6-C_{12})$-aryl; $(C_6-C_{12})$-aryl-$(C_1-C_6)$-alkyl; fluorine, chlorine, bromine, iodine, nitro, cyano, hydroxyl, a sulphone group, a sulphonic acid group, a carboxylic acid ester group or a group —$N^{21}R^{22}$, wherein $R^{21}$ and $R^{22}$ independently of one another are hydrogen or $(C_1-C_4)$-alkyl, it being possible for thealiphatic, cycloaliphatic, araliphatic and aromatic radicals mentioned to be substituted by the carboxylic acid group or salts or amides or esters thereof; the sulphonic acid group or salts or amides or esters thereof; hydroxyl; $(C_1-C_4)$-alkyl; $(C_1-C_4)$-alkoxy; primary, secondary or tertiary amino groups, fluorine, chlorine or bromine, and/or to contain one or more hetero atoms, and it being possible for in each case two of the radicals $R^1$ to $R^4$ or $R^5$ to $R^8$ independently of one another together to form a 5- to 12-membered ring system which is optionally substituted and/or contains one or more hetero atoms.

Alkyl groups can be straight-chain or branched. Alkyl groups $R^1$ to $R^8$ and $R^{11}$ to $R^{14}$ preferably have 1 to 22 carbon atoms. Methyl, ethyl, propyl, butyl, pentyl, hexyl, heptyl, octyl, nonyl, decyl, dodecyl and hexadecyl are particularly preferred. Preferred alkyl groups are also those which are substituted by one or more fluorine atoms, in particular 1 to 33 fluorine atoms.

Acyl $R^9$ or $R^{10}$ is preferably the acetyl, the benzoyl or the naphthoyl group.

$(C_5-C_{12})$-Cycloalkyl can be mononuclear or polynuclear and preferably denotes cyclopentyl or cyclohexyl.

$(C_6-C_{12})$-Aryl can be mononuclear or polynuclear and preferably denotes phenyl, 1-naphthyl, 2-naphthyl or biphenyl. A preferred substituted aryl group is tolyl.

$(C_6-C_{12})$-Aryl-$(C_1-C_6)$-alkyl preferably denotes benzyl.

5- to 12-membered ring systems formed by the radicals $R^{11}$ and $R^{13}$, $R^{11}$ and $R^{15}$ or in each case two of the radicals $R^1$ to $R^4$ and $R^5$ to $R^8$ can be aliphatic or aromatic. They can contain oxygen, sulphur and in particular nitrogen as hereto atoms. They can moreover be mono- or polynuclear.

Preferred ring systems formed by the radicals $R^{11}$ and $R^{13}$ or $R^{11}$ and $R^{15}$ are the pyridine, the piperidine and the imidazoline system.

The radicals $R^1$ to $R^4$ or $R^5$ to $R^8$ moreover preferably from the benzene, naphthalene, biphenyl, tolyl, cyclopentane or cyclohexane system.

p and q preferably denote a number from 1 to 4.

Primary, secondary or tertiary amino groups as substituents of the radicals $R^1$ to $R^8$ and $R^{11}$ to $R^{14}$ are preferably N-mono($C_1-C_4$)alkylamino and N,N-di($C_1-C_4$)-alkylamino.

Acid amide groups as substitutes of the radicals $R^1$ to $R^8$ and $R^{11}$ to $R^{14}$ are preferably phthalimide and naphthalimide.

Sulphonic acid or carboxylic acid ester groups as the radicals $R^1$ to $R^8$ or as substituents of these radicals are preferably $(C_1-C_4)$-alkyl esters.

The substituents $COO^\ominus A^\oplus$ and $COO^\ominus B^\oplus$ in the general formula I can be in any desired position of the particular ring.

The 2,2'- and the 4,4'-position are preferred. The 2,2'-position in connection with m=2 and n=0 is particularly preferred.

X in the general formula II preferably denotes nitrogen or phosphorus, particularly preferably nitrogen. Particularly preferred compounds of the general formula I are those where A⊕=B⊕ and those where A⊕=H⊕. Particularly preferred compounds of the general formula I are also those of the general formula Ia

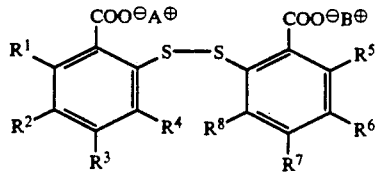

wherein R¹, R³, R⁵ and R⁷ denote hydrogen, R², R⁴, R⁶ and R⁸ denote hydrogen or chlorine and A⊕ and B⊕ have one of the abovementioned meanings.

Especially preferred compounds of the general formula I are those of the general formula Ib

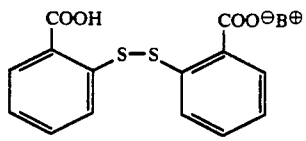

wherein B⊕ denotes tetramethylammonium, tetraethylammonium, tetrapropylammonium, tetrabutylammonium, tetrapentylammonium, tetrahexylammonium, tetraheptylammonium, tetraocytlammonium, tetranonylammonium, tetrakis-(decyl)-ammonium, tetradodecylammonium, tributylmethylammonium, benzyltrimethylammonium, ethylhexadecyldimethylammonium, benzyldimethylhexadecylammonium, benzyltriethylammonium, hexadecyltrimethylammonium, phenyltrimethylammonium, hexadecylpyridinium, guanidinium, 1,1,3,3-tetramethylguanidinium, tetrapropylphosphonium, tetrabutylphosphonium, tetrapentylphosphonium, benzyltriphenylphosphonium or hexadecyltributylphosphonium, those of the general formula Ic

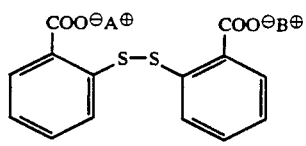

wherein A⊕ and B⊕ are identical and denote tetramethylammonium, tetraethylammonium, tetrapropylammonium, tetrabutylammonium, tetrapentylammonium, tetrahexylammonium, tetraheptylammonium, tetraoctylammonium, tetranonylammonium, tetrakis-(decyl)ammonium, tetradodecylammonium, tributylmethylammonium, benzyltrimethylammonium, ethylhexadecyldimethylammonium, benzyldimethylhexadecylammonium, benzylthriethylammonium, hexadecyltrimethylammonium, methylammonium, phenyltrimethylammonium, hexadecylpyridinium, guanidinium, 1,1,3,3-tetramethylquanidinium, tetrapropylphosphonium, tetrabutylphosphonium, tetrapentylphosphonium, benzyltriphenylphosphonium or hexadecyltributylphosphonium, the compound of the formula Id

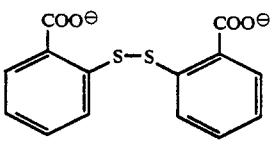

and those of the formula Ie

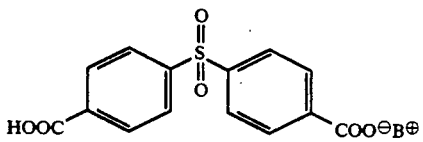

wherein B⊕ denotes tetramethylammonium, tetraethylammonium, tetrapropylammonium, tetrabutylammonium, tetrapentylammonium, tetrahexylammonium, tetraheptylammonium, tetraoctylammonium, tetrapropylphosphonium, or tetrabutylphosphonium.

Examples of the compounds of the general formula I according to the invention are:

2,2'-dithiodibenzoic acid mono-(tetramethylammonium) salt,
2,2'-dithiodibenzoic acid di-(tetramethylammonium) salt,
2,2'-dithiodibenzoic acid mono-(tetraetylammonium) salt,
2,2'-dithiodibenzoic acid di-(tetraethylammonium) salt,
2,2'-dithiodibenzoic acid mono-(tetrapropylammonium) salt,
2,2'-dithiodibenzoic acid di-(tetrapropylammonium) salt,
2,2'-dithiodibenzoic acid di-(tetrapropylammonium) salt,
2,2'-dithiodibenzoic acid di-(tetrabutylammonium) salt,
2,2'-dithiodibenzoic acid mono-(tetrapentylammonium) salt,
2,2'-dithiodibenzoic acid di-(tetrapentylammonium) salt,
2,2'-dithiodibenzoic acid mono-tetrahexylammonium) salt,
2,2'-dithiodibenzoic acid di-(tetrahexylammonium) salt,
2,2'-dithiodibenzoic acid mono-(tetraheptylammonium) salt,
2,2'-dithiodibenzoic acid di-(tetraheptylammonium) salt,
2,2'-dithiodibenzoic acid mono-(tetraoctylammonium) salt,
2,2'-dithiodibenzoic acid di-(tetraoctylammonium) salt,
2,2'-dithiodibenzoic acid mon0-(tetrakis-(decyl)-ammonium) salt
2,2'-dithiodibenzoic acid di-(tetrakis-(decyl)-ammonium) salt
2,2'-dithiodibenzoic acid mono-(tetradodecylammonium) salt
2,2'-dithiodibenzoic acid di-(tetradodecylammonium) salt
2,2'-dithiodibenzoic acid mono-(tributylmethylammonium) salt
2,2'-dithiodibenzoic acid di-(tributylmethylammonium) salt
2,2'-dithiodibenzoic acid mono-(benzyltrimethylammonium) salt
2,2'-dithiodibenzoic acid di-(benzyltrimethylammonium) salt 2,2'-dithiodibenzoic acid mono-(ethylhexadecyldimethylammonium) salt
2,2'-dithiodibenzoic acid di-(ethylhexadecyldimethylammonium) salt
2,2'-dithiodibenzoic acid mono-(benzyldimethylhexadecylammonium) salt
2,2'-dithiodibenzoic acid di-(benzyldimethylhexadecylammonium) salt
2,2'-dithiodibenzoic acid mono-(benzylthriethylammonium) salt
2,2'-dithiodibenzoic acid di-(benzyltriethylammonium) salt
2,2'-dithiodibenzoic acid mono-(hexadecyltrimethylammonium) salt
2,2'-dithiodibenzoic acid di-(hexadecyltrimethylammonium) salt
2,2'-dithiodibenzoic acid mono-(phenyltrimethylammonium) salt
2,2'-dithiodibenzoic acid di-(phenyltrimethylammonium) salt
2,2'-dithiodibenzoic acid mono-(hexadecylpyridinium) salt
2,2'-dithiodibenzoic acid di-(hexadecylpyridinium) salt
2,2'-dithiodibenzoic acid mono-(guanidinium) salt
2,2'-dithiodibenzoic acid di-(guanidinium) salt
2,2'-dithiodibenzoic acid mono-(1,1,3,3-tetramethylguanidinium) salt
2,2'-dithiodibenzoic acid di-(1,1,3,3-tetramethylguanidinium) salt
2,2'-dithiodibenzoic acid mono-(benzyltriphenylphosphonium) salt
2,2'-dithiodibenzoic acid di-(benzyltriphenylphosphonium) salt
2,2'-dithiodibenzoic acid mono-(tetrapropylphosphonium) salt
2,2'-dithiodibenzoic acid di-(tetrapropylphosphonium) salt
2,2'-dithiodibenzoic acid mono-(tetrabutylphosphonium) salt
2,2'-dithiodibenzoic acid di-(tetrabutylphosphonium) salt
2,2'-dithiodibenzoic acid mono-(tetrapentylphosphonium) salt
2,2'-dithiodibenzoic acid di-(tetrapentylphosphonium) salt
2,2'-dithiodibenzoic acid mono-(hexadecyltributylphosphonium) salt
2,2'-dithiodibenzoic acid di-(hexadecyltributylphosphonium) salt
2,2'-dithiodibenzoic acid barium salt
4,4'-dithiodibenzoic acid mono-(tetramethylammonium) salt
4,4'-dithiodibenzoic acid di-(tetramethylammonium) salt
4,4'-dithiodibenzoic acid di-(tetraethylammonium) salt
4,4'-dithiodibenzoic acid mono-(tetrapropylammonium) salt
4,4'-dithiodibenzoic acid di-(tetrapropylammonium) salt
4,4'-dithiodibenzoic acid mono-(tetrabutylammonium) salt
4,4'-dithiodibenzoic acid di-(tetrabutylammonium) salt
4,4'-dithiodibenzoic acid mono-(tetrapentylammonium) salt
4,4'-dithiodibenzoic acid di-(tetrapentylammonium) salt
4,4'-dithiodibenzoic acid mono-(tetrahexylammonium) salt
4,4'-dithiodibenzoic acid di-(tetrahexylammonium) salt
4,4'-dithiodibenzoic acid mono-(tetraheptylammonium) salt
4,4'-dithiodibenzoic acid di-(tetraheptylammonium) salt
4,4'-dithiodibenzoic acid mono-(tetraoctylammonium) salt
4,4'-dithiodibenzoic acid di-(tetraoctylammonium) salt
4,4'-dithiodibenzoic acid mono-(tetrakis-(decyl)-ammonium) salt
4,4'-dithiodibenzoic acid di-(tetrakis-(decyl)-ammonium) salt
4,4'-dithiodibenzoic acid mono-(tetradodecylammonium) salt
4,4'-dithiodibenzoic acid di-(tetradodecylammonium) salt
4,4'-dithiodibenzoic acid mono-(tributylmethylammonium) salt
4,4'-dithiodibenzoic acid di-(tributylmethylammonium) salt
4,4'-dithiodibenzoic acid mono-(benzyltrimethylammonium) salt
4,4'-dithiodibenzoic acid di-(benzyltrimethylammonium) salt
4,4'-dithiodibenzoic acid mono-(ethylhexadecyldimethylammonium) salt
4,4'-dithiodibenzoic acid di-(ethylhexadecyldimethylammonium) salt
4,4'-dithiodibenzoic acid mono-(benzyldimethylhexadecylammonium) salt
4,4'-dithiodibenzoic acid di-(benzyldimethylhexadecylammonium) salt
4,4'-dithiodibenzoic acid mono-(benzyltriethylammonium) salt
4,4'-dithiodibenzoic acid di-(benzyltriethylammonium) salt
4,4'-dithiodibenzoic acid mono-(hexadecyltrimethylammonium) salt
4,4'-dithiodibenzoic acid di-(hexadecyltrimethylammonium) salt
4,4'-dithiodibenzoic acid mono-(phenyltrimethylammonium) salt
4,4'-dithiodibenzoic acid di-(phenyltrimethylammonium) salt
4,4'-dithiodibenzoic acid mono-(hexadecylpyridinium) salt
4,4'-dithiodibenzoic acid di-(hexadecylpyridinium) salt
4,4'-dithiodibenzoic acid mono-(guanidinium) salt
4,4'-dithiodibenzoic acid di-(guanidinium) salt
4,4'-dithiodibenzoic acid mono-(benzyltriphenylphosphonium) salt
4,4'-dithiodibenzoic acid di-(benzyltriphenylphosphonium) salt
4,4'-dithiodibenzoic acid mono-(tetrabutylphosphonium) salt
4,4'-dithiodibenzoic acid di-(tetrabutylphosphonium) salt
4,4'-dithiodibenzoic acid mono-(hexadecyltributylphosphonium) salt
4,4'-dithiodibenzoic acid di-(hexadecyltributylphosphonium) salt
4,4'-dithiodibenzoic acid barium salt
2,2'-thiodibenzoic acid mono-(tetramethylammonium) salt
2,2'-thiodibenzoic acid di-(tetramethylammonium) salt
2,2'-thiodibenzoic acid mono-(tetraethylammonium) salt
2,2'-thiodibenzoic acid di-(tetraethylammonium) salt
2,2'-thiodibenzoic acid mono-(tetrapropylammonium) salt 2,2'-thiodibenzoic acid di-(tetrapropylammonium) salt
2,2'-thiodibenzoic acid mono-(tetrabutylammonium) salt
2,2'-thiodibenzoic acid di-(tetrabutylammonium) salt
2,2'-thiodibenzoic acid mono-(tetrapentylammonium) salt
2,2'-thiodibenzoic acid di-(tetrapentylammonium) salt
2,2'-thiodibenzoic acid mono-(tetrahexylammonium) salt
2,2'-thiodibenzoic acid di-(tetrahexylammonium) salt
2,2'-thiodibenzoic acid mono-(tetraheptylammonium) salt
2,2'-thiodibenzoic acid di-(tetraheptylammonium) salt
2,2'-thiodibenzoic acid mono-(tetraoctylammonium) salt
2,2'-thiodibenzoic acid di-(tetraoctylammonium) salt
2,2'-thiodibenzoic acid mono-(tetrakis-(decyl)-ammonium) salt
2,2'-thiodibenzoic acid di-(tetrakis-(decyl)-ammonium) salt
2,2'-thiodibenzoic acid mono-(tetradodecylammonium) salt
2,2'-thiodibenzoic acid di-(tetradodecylammonium) salt
2,2'-thiodibenzoic acid mono-(tributylmethylammonium) salt
2,2'-thiodibenzoic acid di-(tributylmethylammonium) salt
2,2'-thiodibenzoic acid mono-(benzyltrimethylammonium) salt
2,2'-thiodibenzoic acid di-(benzyltrimethylammonium) salt
2,2'-thiodibenzoic acid mono-(ethylhexadecyldimethylammonium) salt
2,2'-thiodibenzoic acid di-(ethylhexadecyldimethylammonium) salt
2,2'-thiodibenzoic acid mono-(benzyldimethylhexadecylammonium) salt
2,2'-thiodibenzoic acid di-(benzyldimethylhexadecylammonium) salt
2,2'-thiodibenzoic acid mono-(benzyltriethylammonium) salt
2,2'-thiodibenzoic acid di-(benzyltriethylammonium) salt
2,2'-thiodibenzoic acid mono-(hexadecyltrimethylammonium) salt
2,2'-thiodibenzoic acid di-(hexadecyltrimethylammonium) salt
2,2'-thiodibenzoic acid mono-(phenyltrimethylammonium) salt
2,2'-thiodibenzoic acid di-(phenyltrimethylammonium) salt
2,2'-thiodibenzoic acid mono-(hexadecylpyridinium) salt
2,2'-thiodibenzoic acid di-(hexadecylpyridinium) salt
2,2'-thiodibenzoic acid mono-(guanidinium) salt
2,2'-thiodibenzoic acid di-(guanidinium) salt
2,2'-thiodibenzoic acid mono-(benzyltriphenylphosphonium) salt
2,2'-thiodibenzoic acid di-(benzyltriphenylphosphonium) salt
2,2'-thiodibenzoic acid mono-(tetrabutylphosphonium) salt
2,2'-thiodibenzoic acid di-(tetrabutylphosphonium) salt
2,2'-thiodibenzoic acid mono-(hexadecyltributylphosphonium) salt
2,2'-thiodibenzoic acid di-(hexadecyltributylphosphonium) salt
2,2'-thiodibenzoic acid barium salt 4,4'-thiodibenzoic acid mono-(tetramethylammonium) salt
4,4'-thiodibenzoic acid di-(tetramethylammonium) salt
4,4'-thiodibenzoic acid mono-(tetraethylammonium) salt
4,4'-thiodibenzoic acid di-(tetraethylammonium) salt
4,4'-thiodibenzoic acid mono-(tetrapropylammonium) salt
4,4'-thiodibenzoic acid di-(tetrapropylammonium) salt
4,4'-thiodibenzoic acid mono-(tetrabutylammonium) salt
4,4'-thiodibenzoic acid di-(tetrabutylammonium) salt
4,4'-thiodibenzoic acid mono-(tetrapentylammonium) salt
4,4'-thiodibenzoic acid di-(tetrapentylammonium) salt
4,4'-thiodibenzoic acid mono-(tetrahexylammonium) salt
4,4'-thiodibenzoic acid di-(tetrahexylammonium) salt
4,4'-thiodibenzoic acid mono-(tetraheptylammonium) salt
4,4'-thiodibenzoic acid di-(tetraheptylammonium) salt
4,4'-thiodibenzoic acid mono-(tetraoctylammonium) salt
4,4'-thiodibenzoic acid di-(tetraoctylammonium) salt
4,4'-thiodibenzoic acid mono-(tetrakis-(decyl)-ammonium) salt
4,4'-thiodibenzoic acid di-(tetrakis-(decyl)-ammonium) salt
4,4'-thiodibenzoic acid mono-(tetradodecylammonium) salt
4,4'-thiodibenzoic acid di-(tetradodecylammonium) salt
4,4'-thiodibenzoic acid mono-(tributylmethylammonium) salt
4,4'-thiodibenzoic acid di-(tributylmethylammonium) salt
4,4'-thiodibenzoic acid mono-(benzyltrimethylammonium) salt
4,4'-thiodibenzoic acid di-(benzyltrimethylammonium) salt
4,4'-thiodibenzoic acid mono-(ethylhexadecyldimethylammonium) salt
4,4'-thiodibenzoic acid di-(ethylhexadecyldimethylammonium) salt
4,4'-thiodibenzoic acid mono-(benzyldimethylhexadecylammonium) salt
4,4'-thiodibenzoic acid mono-(benzyldimethylhexadecylammonium) salt
4,4'-thiodibenzoic acid di-(benzyldimethylhexadecylammonium) salt
4,4'-thiodibenzoic acid mono-(benzyltriethylammonium) salt
4,4'-thiodibenzoic acid di-(benzyltriethylammonium) salt
4,4'-thiodibenzoic acid mono-(hexadecyltrimethylammonium) salt
4,4'-thiodibenzoic acid di-(hexadecyltrimethylammonium) salt
4,4'-thiodibenzoic acid mono-(phenyltrimethylammonium) salt
4,4'-thiodibenzoic acid di-(phenyltrimethylammonium) salt
4,4'-thiodibenzoic acid mono-(hexadecylpyridinium) salt
4,4'-thiodibenzoic acid di-(hexadecylpyridinium) salt
4,4'-thiodibenzoic acid mono-(guanidinium) salt
4,4'-thiodibenzoic acid di-(guanidinium) salt 4,4'-thiodibenzoic acid mono-(benzyltriphenylphosphonium) salt
4,4'-thiodibenzoic acid di-(benzyltriphenylphosphonium) salt
4,4'-thiodibenzoic acid mono-(tetrabutylphosphonium) salt
4,4'-thiodibenzoic acid di-(tetrabutylphosphonium) salt
4,4'-thiodibenzoic acid mono-(hexadecyltributylphosphonium) salt
4,4'-thiodibenzoic acid di-(hexadecyltributylphosphonium) salt
4,4'-thiodibenzoic acid barium salt
2,2'-sulphinyldibenzoic acid mono-(tetramethylammonium) salt
2,2'-sulphinyldibenzoic acid di-(tetramethylammonium) salt
2,2'-sulphinyldibenzoic acid mono-(tetraethylammonium) salt
2,2'-sulphinyldibenzoic acid di-(tetraethylammonium) salt
2,2'-sulphinyldibenzoic acid mono-(tetrapropylammonium) salt
2,2'-sulphinyldibenzoic acid di-(tetrapropylammonium) salt
2,2'-sulphinyldibenzoic acid mono-(tetrabutylammonium) salt
2,2'-sulphinyldibenzoic acid di-(tetrabutylammonium) salt
2,2'-sulphinyldibenzoic acid mono-(tetrapentylammonium) salt
2,2'-sulphinyldibenzoic acid di-(tetrapentylammonium) salt
2,2'-sulphinyldibenzoic acid mono-(tetrahexylammonium) salt
2,2'-sulphinyldibenzoic acid di-(tetrahexylammonium) salt
2,2'-sulphinyldibenzoic acid mono-(tetraheptylammonium) salt
2,2'-sulphinyldibenzoic acid di-(tetraheptylammonium) salt
2,2'-sulphinyldibenzoic acid mono-(tetraoctylammonium) salt
2,2'-sulphinyldibenzoic acid di-(tetraoctylammonium) salt
2,2'-sulphinyldibenzoic acid mono-(tetrakis-(decyl)-ammonium) salt
2,2'-sulphinyldibenzoic acid di-(tetrakis-(decyl)-ammonium) salt
2,2'-sulphinyldibenzoic acid mono-(tetradodecylammonium) salt
2,2'-sulphinyldibenzoic acid di-(tetradodecylammonium) salt
2,2'-sulphinyldibenzoic acid mono-(tributylmethylammonium) salt
2,2'-sulphinyldibenzoic acid di-(tributylmethylammonium) salt
2,2'-sulphinyldibenzoic acid mono-(benzyltrimethylammonium) salt
2,2'-sulphinyldibenzoic acid di-(benzyltrimethylammonium) salt
2,2'-sulphinyldibenzoic acid mono-(ethylhexadecyldimethylammonium) salt
2,2'-sulphinyldibenzoic acid di-(ethylhexadecyldimethylammonium) salt
2,2'-sulphinyldibenzoic acid mono-(benzyldimethylhexadecylammonium) salt
2,2'-sulphinyldibenzoic acid di-(benzyldimethylhexadecylammonium) salt
2,2'-sulphinyldibenzoic acid mono-(benzyltriethylammonium) salt
2,2'-sulphinyldibenzoic acid di-(benzyltriethylammonium) salt
2,2'-sulphinyldibenzoic acid mono-(hexadecyltrimethylammonium) salt
2,2'-sulphinyldibenzoic acid di-(hexadecyltrimethylammonium) salt
2,2'-sulphinyldibenzoic acid mono-(phenyltrimethylammonium) salt
2,2'-sulphinyldibenzoic acid di-(phenyltrimethylammonium) salt
2,2'-sulphinyldibenzoic acid mono-(hexadecylpyridinium) salt
2,2'-sulphinyldibenzoic acid di-(hexadecylpyridinium) salt
2,2'-sulphinyldibenzoic acid mono-(guanidinium) salt
2,2'-sulphinyldibenzoic acid di-(quanidinium) salt
2,2'-sulphinyldibenzoic acid mono-(benzyltriphenylphosphonium) salt
2,2'-sulphinyldibenzoic acid di-(benzyltriphenylphosphonium) salt
2,2'-sulphinyldibenzoic acid mono-(tetrabutylphosphonium) salt
2,2'-sulphinyldibenzoic acid di-(tetrabutylphosphonium) salt
2,2'-sulphinyldibenzoic acid mono-(hexadecyltributylphosphonium) salt
2,2'-sulphinyldibenzoic acid di-(hexadecyltributylphosphonium) salt
2,2'-sulphinyldibenzoic acid barium salt
4,4'-sulphinyldibenzoic acid mono-(tetramethylammonium) salt
4,4'-sulphinyldibenzoic acid di-(tetramethylammonium) salt
4,4'-sulphinyldibenzoic acid mono-(tetraethylammonium) salt
4,4'-sulphinyldibenzoic acid di-(tetraethylammonium) salt
4,4'-sulphinyldibenzoic acid mono-(tetrapropylammonium) salt
4,4'-sulphinyldibenzoic acid di-(tetrapropylammonium) salt
4,4'-sulphinyldibenzoic acid mono-(tetrabutylammonium) salt
4,4'-sulphinyldibenzoic acid di-(tetrabutylammonium) salt
4,4'-sulphinyldibenzoic acid mono-(tetrapentylammonium) salt
4,4'-sulphinyldibenzoic acid di-(tetrapentylammonium) salt
4,4'-sulphinyldibenzoic acid mono-(tetrahexylammonium) salt
4,4'-sulphinyldibenzoic acid di-(tetrahexylammonium) salt
4,4'-sulphinyldibenzoic acid mono-(tetraheptylammonium) salt
4,4'-sulphinyldibenzoic acid di-(tetraheptylammonium) salt
4,4'-sulphinyldibenzoic acid mono-(tetraoctylammonium) salt
4,4'-sulphinyldibenzoic acid di-(tetraoctylammonium) salt
4,4'-sulphinyldibenzoic acid mono-(tetrakis-(decyl)-ammonium) salt
4,4'-sulphinyldibenzoic acid di-(tetrakis-(decyl)-ammonium) salt 4,4'-sulphinyldibenzoic acid mono-(tetradodecylammonium) salt
4,4'-sulphinyldibenzoic acid di-(tetradodecylammonium) salt
4,4'-sulphinyldibenzoic acid mono-(tributylmethylammonium) salt
4,4'-sulphinyldibenzoic acid di-(tributylmethylammonium) salt
4,4'-sulphinyldibenzoic acid mono-(benzyltrimethylammonium) salt
4,4'-sulphinyldibenzoic acid di-(benzyltrimethylammonium) salt
4,4'-sulphinyldibenzoic acid mono-(ethylhexadecyldimethylammonium) salt
4,4'-sulphinyldibenzoic acid di-(ethylhexadecyldimethylammonium) salt
4,4'-sulphinyldibenzoic acid mono-(benzyldimethylhexadecylammonium) salt
4,4'-sulphinyldibenzoic acid di-(benzyldimethylhexadecylammonium) salt
4,4'-sulphinyldibenzoic acid mono-(benzyltriethylammonium) salt
4,4'-sulphinyldibenzoic acid di-(benzyltriethylammonium) salt
4,4'-sulphinyldibenzoic acid mono-(hexadecyltrimethylammonium) salt
4,4'-sulphinyldibenzoic acid di-(hexadecyltrimethylammonium) salt
4,4'-sulphinyldibenzoic acid mono-(phenyltrimethylammonium) salt
4,4'-sulphinyldibenzoic acid di-(phenyltrimethylammonium) salt
4,4'-sulphinyldibenzoic acid mono-(hexadecylpyridinium) salt
4,4'-sulphinyldibenzoic acid di-(hexadecylpyridinium) salt
4,4'-sulphinyldibenzoic acid mono-(guanidinium) salt
4,4'-sulphinyldibenzoic acid di-(quanidinium) salt
4,4'-sulphinyldibenzoic acid mono-(benzyltriphenylphosphonium) salt
4,4'-sulphinyldibenzoic acid di-(benzyltriphenylphosphonium salt
4,4'-sulphinyldibenzoic acid mono-(tetrabutylphosphonium) salt
4,4'-sulphinyldibenzoic acid di-(tetrabutylphosphonium) salt
4,4'-sulphinyldibenzoic acid mono-(hexadecyltributylphosphonium) salt
4,4'-sulphinyldibenzoic acid di-(hexadecyltributylphosphonium) salt
4,4'-sulphinyldibenzoic acid barium salt
2,2'-sulphonyldibenzoic acid mono-(tetramethylammonium) salt
2,2'-sulphonyldibenzoic acid di-(tetramethylammonium) salt
2,2'-sulphonyldibenzoic acid mono-(tetraethylammonium) salt
2,2'-sulphonyldibenzoic acid di-(tetraethylammonium) salt
2,2'-sulphonyldibenzoic acid mono-(tetrapropylammonium) salt
2,2'-sulphonyldibenzoic acid di-(tetrapropylammonium) salt
2,2'-sulphonyldibenzoic acid mono-(tetrabutylammonium) salt
2,2'-sulphonyldibenzoic acid di-(tetrabutylammonium) salt
2,2'-sulphonyldibenzoic acid mono-(tetrapentylammonium) salt
2,2'-sulphonyldibenzoic acid di-(tetrapentylammonium) salt
2,2'-sulphonyldibenzoic acid mono-(tetrahexylammonium) salt
2,2'-sulphonyldibenzoic acid di-(tetrahexylammonium) salt
2,2'-sulphonyldibenzoic acid mono-(tetraheptylammonium) salt
2,2'-sulphonyldibenzoic acid di-(tetraheptylammonium) salt
2,2'-sulphonyldibenzoic acid mono-(tetraoctylammonium) salt
2,2'-sulphonyldibenzoic acid di-(tetraoctylammonium) salt
2,2'-sulphonyldibenzoic acid mono-(tetrakis-(decyl)-ammonium) salt
2,2'-sulphonyldibenzoic acid di-(tetrakis-(decyl)-ammonium) salt
2,2'-sulphonyldibenzoic acid mono-(tetradodecylammonium) salt
2,2'-sulphonyldibenzoic acid di-(tetradodecylammonium) salt
2,2'-sulphonyldibenzoic acid mono-(tributylamethylammonium) salt
2,2'-sulphonyldibenzoic acid di-(tributylmethylammonium) salt
2,2'-sulphonyldibenzoic acid mono-(benzyltrimethylammonium) salt
2,2'-sulphonyldibenzoic acid di-(benzyltrimethylammonium) salt
2,2'-sulphonyldibenzoic acid mono-(ethylhexadecyldimethylammonium) salt
2,2'-sulphonyldibenzoic acid di-(ethylhexadecyldimethylammonium) salt
2,2'-sulphonyldibenzoic acid mono-(benzyldimethylhexadecylammonium) salt
2,2'-sulphonyldibenzoic acid di-(benzyldimethylhexadecylammonium) salt
2,2'-sulphonyldibenzoic acid mono-(benzyltriethylammonium) salt
2,2'-sulphonyldibenzoic acid di-(benzyltriethylammonium) salt
2,2'-sulphonyldibenzoic acid mono-(hexadecyltrimethylammonium) salt
2,2'-sulphonyldibenzoic acid di-(hexadecyltrimethylammonium) salt
2,2'-sulphonyldibenzoic acid mono-(phenyltrimethylammonium) salt
2,2'-sulphonyldibenzoic acid di-(phenyltrimethylammonium) salt
2,2'-sulphonyldibenzoic acid mono-(hexadecylpyridinium) salt
2,2'-sulphonyldibenzoic acid di-(hexadecylpyridinium) salt
2,2'-sulphonyldibenzoic acid mono-(guanidinium) salt
2,2'-sulphonyldibenzoic acid di-(guanidinium) salt
2,2'-sulphonyldibenzoic acid mono-(benzyltriphenylphosphonium) salt
2,2'-sulphonyldibenzoic acid di-(benzyltriphenylphosphonium) salt
2,2'-sulphonyldibenzoic acid mono-(tetrabutylphosphonium) salt
2,2'-sulphonyldibenzoic acid di-(tetrabutylphosphonium) salt
2,2'-sulphonyldibenzoic acid mono-(hexadecyltributylphosphonium) salt 2,2'-sulphonyldibenzoic acid di-(hexadecyltributylphosphonium) salt
2,2'-sulphonyldibenzoic acid barium salt
4,4'-sulphonyldibenzoic acid mono-(tetramethylammonium) salt
4,4'-sulphonyldibenzoic acid di-(tetramethylammonium) salt
4,4'-sulphonyldibenzoic acid mono-(tetraethylammonium) salt
4,4'-sulphonyldibenzoic acid di-(tetraethylammonium) salt
4,4'-sulphonyldibenzoic acid mono-(tetrapropylammonium) salt
4,4'-sulphonyldibenzoic acid di-(tetrapropylammonium) salt
4,4'-sulphonyldibenzoic acid mono-(tetrabutylammonium) salt
4,4'-sulphonyldibenzoic acid di-(tetrabutylammonium) salt
4,4'-sulphonyldibenzoic acid mono-(tetrapentylammonium) salt
4,4'-sulphonyldibenzoic acid di-(tetrapentylammonium) salt
4,4'-sulphonyldibenzoic acid mono-(tetrahexylammonium) salt
4,4'-sulphonyldibenzoic acid di-(tetrahexylammonium) salt
4,4'-sulphonyldibenzoic acid mono-(tetraheptylammonium) salt
4,4'-sulphonyldibenzoic acid di-(tetraheptylammonium) salt
2,4'-sulphonyldibenzoic acid mono-(tetraoctylammonium) salt
4,4'-sulphonyldibenzoic acid di-(tetraoctylammonium) salt
4,4'-sulphonyldibenzoic acid mono-(tetrakis-(decyl)-ammonium) salt
4,4'-sulphonyldibenzoic acid di-(tetrakis-(decyl)-ammonium) salt
4,4'-sulphonyldibenzoic acid mono-(tetradodecylammonium) salt
4,4'-sulphonyldibenzoic acid di-(tetradodecylammonium) salt
4,4'-sulphonyldibenzoic acid mono-(tributylmethylammonium) salt
4,4'-sulphonyldibenzoic acid di-(tributylmethylammonium) salt
4,4'-sulphonyldibenzoic acid mono-(benzyltrimethylammonium) salt
4,4'-sulphonyldibenzoic acid di-(benzyltrimethylammonium) salt
4,4'-sulphonyldibenzoic acid mono-(ethylhexadecyldimethylammonium) salt
4,4'-sulphonyldibenzoic acid di-(ethylhexadecyldimethylammonium) salt
4,4'-sulphonyldibenzoic acid mono-(benzyldimethylhexadecylammonium) salt
4,4'-sulphonyldibenzoic acid di-(benzyldimethylhexadecylammonium) salt
4,4'-sulphonyldibenzoic acid mono-(benzyltriethylammonium) salt
4,4'-sulphonyldibenzoic acid di-(benzyltriethylammonium) salt
4,4'-sulphonyldibenzoic acid mono-(hexadecyltrimethylammonium) salt
4,4'-sulphonyldibenzoic acid di-(hexadecyltrimethylammonium) salt
4,4'-sulphonyldibenzoic acid mono-(phenyltrimethylammonium) salt
4,4'-sulphonyldibenzoic acid di-(phenyltrimethylammonium) salt
4,4'-sulphonyldibenzoic acid mono-(hexadecylpyridinium) salt
4,4'-sulphonyldibenzoic acid di-(hexadecylpyridinium) salt
4,4'-sulphonyldibenzoic acid mono-(guanidinium) salt
4,4'-sulphonyldibenzoic acid di-(guanidinium) salt
4,4'-sulphonyldibenzoic acid mono-(benzyltriphenylphosphonium) salt
4,4'-sulphonyldibenzoic acid di-(benzyltriphenylphosphonium) salt
4,4'-sulphonyldibenzoic acid mono-(tetrabutylphosphonium) salt
4,4'-sulphonyldibenzoic acid di-(tetrabutylphosphonium) salt
4,4'-sulphonyldibenzoic acid mono-(hexadecyltributylphosphonium) salt
4,4'-sulphonyldibenzoic acid di-(hexadecyltributylphosphonium) salt
4,4'-sulphonyldibenzoic acid barium salt The compounds of the general formula I according to the invention can be prepared by reaction by reaction of the compounds of the general formula V

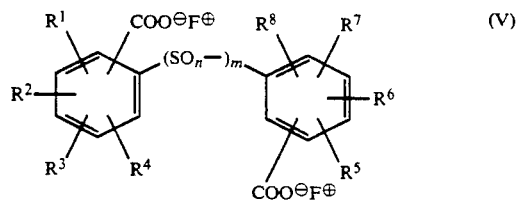

wherein $R^1$ to $R^8$ and m and n have the abovementioned meaning and $E^\oplus$ and $F^\oplus$ independently of one another represent a proton, an alkali metal ion or the ammonium ion, with a compound of the formula $A^\oplus Y_a^\ominus$, or $B^\oplus Y_b^\oplus$, or a mixture of the two compounds, wherein $Y_a^\ominus$ and $Y_b^\ominus$ independently of one another denote an anion or an anion equivalent and $A^\oplus$ and $B^\oplus$ have the abovementioned meaning, the proton being excluded.

An alkali metal $E^\oplus$ or $F^\oplus$ is preferably the sodium or the potassium ion.

Anions $Y_a^\ominus$ and $Y_b^\oplus$ are preferably hydroxide, carbonate, bicarbonate, chloride, bromide, iodide, tetrafluoroborate, tosylate, sulphate, or hydrogen sulphate.

In a preferred embodiment of the process according to the invention, the reaction is carried out with hydroxides AOH or BOH, a solvent in which both the hydroxide and the reaction product are soluble being chosen. Solvents of this type are organic solvents, alcohols, such as, for example, methanol, ethanol, 1-propanol and 2-propanol and mixtures thereof with water being particularly suitable, $E^\oplus$ and $E^\oplus$ represent a proton here. The starting compounds are employed in this reaction in stoichiometric amounts, and the products, which are obtained in a pure form in the theoretical yield, can be obtained from the mixture directly by concentration and subsequent drying.

The reaction temperature is not critical here. The reaction is advantageously carried out in the temperature range between room temperature and the boiling point of the reaction mixture.

In another preferred embodiment, the process according to the invention is carried out in accordance with the principle of a precipitation reaction. Any solvent or solvent mixture which does not participate in the reaction and in which a di(alkali metal) salt or the diammonium salt of the compound of the general formula V is soluble but the product of the general formula I according to the invention is insoluble is in principle suitable as the reaction medium. Water is as a rule particularly suitable as the reaction medium.

A procedure is advantageously followed in which the compound of the general formula V wherein $E^{\oplus}$ and $F^{\oplus}$ represent a proton is dissolved in water with the calculated amount of alkali metal hydroxide or ammonium hydroxide to give the di(alkali metal) or diammonium salt, and a compound of the formula $A^{\oplus}Y_a^{\ominus}$ or $B^{\oplus}Y_b^{\ominus}$, or a mixture of the two compounds, preferably in dissolved form, is added. Products of the general formula I according to the invention which are insoluble in water precipitate out by this procedure and can be isolated by filtration.

The temperature is also not critical in this process. It is advantageously between 5° and 95° C.

If a di-salt of the general formula I according to the invention is soluble in the reaction medium but the corresponding mono-salt is insoluble, the latter can be precipitated in a simple manner by addition of acid to a solution of the di(alkali metal) or diammonium salt of the general formula V and of a neutral salt $A^{\oplus}Y_a^{\ominus}$ or $B^{\oplus}Y_b^{-}$ and can be isolated by filtration.

If, however, $Y_a^{-}$ or $Y_b^{\oplus}$ represents a monobasic acid anion, for example hydrogen sulphate, the insoluble mono-salt according to the inventional ready precipitates out an addition of $A^{\oplus}Y_a^{\ominus}$ or $B^{\oplus}Y_b^{\ominus}$ to the solution of the di(alkali metal) or diammonium salt of the general formula V. In this case, not more than the stoichiometric amount of $A^{\oplus}Y_a^{\ominus}$ or $B^{\oplus}Y_b^{\ominus}$ is advantageously employed, in order to avoid an excess of acid anoin. In the case of neutral anions, the stoichiometric amount or a small excess of $A^{\oplus}Y_a^{\ominus}$ or $B^{\oplus}Y_b^{\ominus}$ is advantageously employed in order to achieve a good yield.

The acid used for the precipitation must be sufficiently strong. Examples of suitable acids are sulphuric acid, hydrochloric acid and formic acid.

Not more than the stoichiometric amount of acid is advantageously used for precipitation of mono-salts of the general formula I. Too little acid reduces the yield, and too much acid causes contamination of the product with the corresponding dibenzoic acid.

The insoluble mono-salts of the general formula I can in principle also be obtained by a procedure in which a solution of the compound $A^{\oplus}Y_a^{\ominus}$ or $B^{\oplus}Y_b^{\ominus}$ wherein $Y_a^{\ominus}$ or $Y_b^{\oplus}$ represents a neutral anion is added to a solution of a mono(alkali metal) or monoammonium salt of the general formula V. Although the desired product also precipitates out, this procedure has the serious disadvantage in practice that considerably higher dilutions are necessary for the complete dissolution of a mono(alkali metal) salt or a monoammonium salt to achieve a smooth reaction.

An especially preferred process is a process for the preparation of sparingly water-soluble mono-salts of dithiodibenzoic acids with quaternary nitrogen or phosphorus bases, of the general formula if

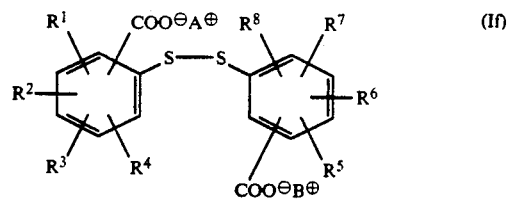

wherein $A^{\oplus}$ and $B^{\oplus}$ denote a proton or an ion of the general formula II

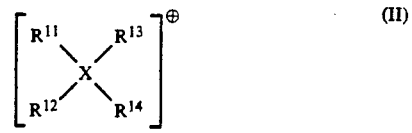

wherein either $A^{\oplus}$ or $B^{\ominus}$ represents a proton; X denotes nitrogen or phosphorus and $R^1$ and $R^8$ and $R^{11}$ to $R^{14}$ are as defined above, characterised in that the compound of the general formula I is precipitated, by means of carbon dioxide, from an aqueous solution which contains equimolar amounts of a compound of the general formula Va

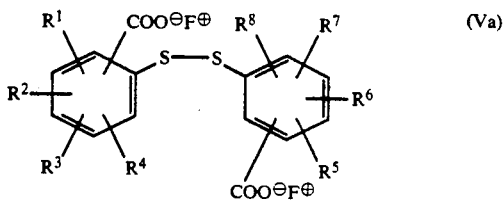

wherein $R^1$ to $R^8$ are as defined above and $E^{\oplus}$ and $F^{\oplus}$ independently of one another represent an alkali metal ion or the ammonium ion, and a compound $A^{\oplus}Y_b^{\ominus}$, wherein $A^{\oplus}$ and $B^{\oplus}$ represent an ion of the general formula II and $Y_a^{\oplus}$ and $Y_b^{\oplus}$ denote an anion or anion equivalent.

This process is particularly advantageous for the preparation of salts of 2,2'-dithiodibenzoic acid with ions of the general formula II, wherein X denotes nitrogen or phosphorus and $R^{11}$ and to $R^{14}$ denote n-propyl or n-butyl.

The compound of the general formula I is preferably precipitated by passing in gaseous carbon dioxide. Carbon dioxide is preferably passed in here up to a pH of 6.0 to 9.0, particularly preferably 7.0 to 8.0.

The temperature is not critical and is preferably between 5° and 95° C.

The precipitated product can be isolated and dried in a simple manner which is known per se.

The compounds of the formulae $A^{\oplus}Y_a^{\ominus}$ and $B^{\oplus}Y_b^{\ominus}$ are commercially obtainable and/or can be prepared by methods known to the expert.

The compounds of the general formula V wherein $E^{\oplus}$ and $F^{\oplus}$ represent a proton are known from the literature and are described, for example, in the following literature references:

2,2'-dithiodibenzoic acid: ORGANIC SYNTHESIS Collective Volume 2 (1943), 580, D.R.P. 601642 and German Offenlegungsschrift 3,201,904

3,3'-dithiodibenzoic acid: J. Pharm. Soc. Japan 77 (1957), 965, 968

4,4'-dithiodibenzoic acid: Journal of the Chemical Society Transaction 1922, Volume 121, 2025, J. Soc. Chem. Ind. 44, 196 T and J. Heterocyclic Chem., 17, 497 (1980)

2,2'-thiodibenzoic acid: Berichte der deutschem chemischen Gesellschaft, 43 (1910), 588 and U.S. Pat. No. 3,997,540

4,4'-thiodibenzoic acid: J. Pharm. Soc. Japan 64 (1944) 186, 189 USSR 722,906 and U.S. Pat. No. 3,504,002

2,2'-sulphinyldibenzoic acid: Berichte der deutschen chemischen Gesellschaft, 43 (1910), 589 and The Journal of the American Chemical Society, Volume 75 (1953), 280, 281, 4,4'-sulphinyldibenzoic acid: U.S. Pat. No. 3,504,022

2,2'-sulphonyldibenzoic acid: The Journal of the American Chemical Society, Volume 75 (1953), 280, 281

4,4'-sulphonyldibenzoic acid: U.S. Pat. No. 2,614,120, U.S. Pat. No. 2,637,218 and Acta Chem. Scand. 7 (1953) No. 5, 778

Compounds of the general formula V in which $R^1$ to $R^8$ have meanings other than hydrogen can be prepared in an analogous manner. The alkali metal or ammonium salts of the compounds of the general formula V can be prepared in a simple manner from the acid forms by reaction with alkali metal hydroxide or ammonium hydroxide.

As well as being present in the pure form, the compounds of the general formula I according to the invention can also be present in the form of mixtures and mixed crystals with one another, and in the form of mixtures and mixed crystals containing up to 90% by weight of the compounds of the general formula V wherein $E^\oplus$ and $F^\oplus$ represent a proton.

The present invention therefore also relates to mixtures and mixed crystals of a) 10 to 100% by weight of one or more compounds of the general formula I

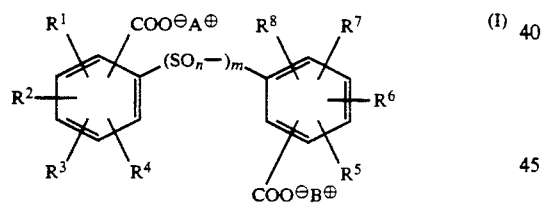

wherein $R^1$ to $R^8$, $A^\oplus$, $B^\oplus$ and m and n are as defined above, and b) 0 to 90% by weight of one or more compounds of the general formula V

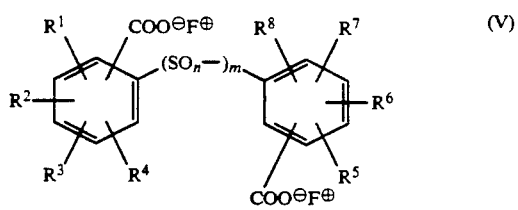

wherein $R^1$ to $R^8$ and m and n are as defined above and $E^\oplus$ and $F^\oplus$ represent a proton.

Preferred mixtures and mixed crystals are those of two compounds of the general formula I, mixtures and mixed crystals of the di-salt and mono-salt being particularly preferred. The di-salt and mono-salt are identical here in respect of $R^1$ to $R^8$, m, and n $A^\oplus$, and differ only in that in one compound $B^\oplus = A^\oplus$ and in the other component $B^\oplus = H^\oplus$.

Mixtures and mixed crystals of a compound of the general formula I where $A^\oplus = H^\oplus$ which contain less than 50% by weight, particularly preferably less than 20% by weight, of the corresponding compound of the general formula V wherein $E^\oplus$ and $F^\oplus$ represent a proton are also preferred.

The mixtures according to the invention can be prepared by simple mixing of the corresponding amounts of the individual constituents.

However, mixtures and mixed crystals according to the invention can also be obtained by processes analogous to those described above for the individual compounds, corresponding mixtures of starting compounds being employed or an excess of acid being used.

The compounds according to the invention are outstandingly suitable for use as colourless charge control agents in toners and developers for electrophotographic recording processes and for use as charge improving agents in powders and varnishes for surface coating, in particular in powder varnishes sprayed tribo-electrically or electrokinetically.

All the melting point data in the following examples are uncorrected.

EXAMPLE 1

30.6 g of 2,2'dithiodibenzoic acid (0.10 mol) are suspended in 600 ml of ethanol. 36.5 g of a 25% strength aqueous tetramethylammonium hydroxide solution (0.10 mol) are slowly added dropwise to those suspension at 70°-75° C., while stirring. On concentrating, a moist crystal mass separates out of the reaction solution, which is dried in a through-circulation drying cabinet at 120° C. and then ground.

Yield: 37.8 g (99.6% of theory) of 2,2'-dithiodibenzoic acid mono(tetramethylammonium) salt of the formula

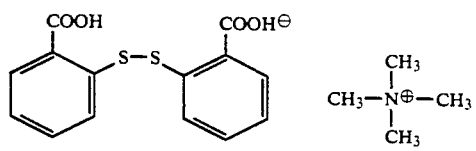

$C_{18}H_{21}NO_4S_2$ molecular weight: 379.49
White powder
Melting point: 240° C.
1H-NMR (in DMSO-$d_6$): δ3.15 (s, 12H), 7.1–8.1 (m, 8H$_{ar}$.)

EXAMPLE 2

The procedure is as in Example 1, with the difference that 72.9 g of a 25% strength aqueous tetramethylammonium hydroxide solution (0.20 mol) are added. Yield: 45.2 g (99.9% of theory)

2,2'-Dithiodibenzoic acid di(tetramethylammonium) salt of the formula

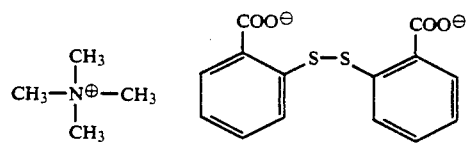

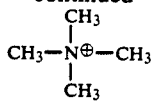

$C_{22}H_{32}N_2O_4S_2$ molecular weight: 452.63
White powder
Melting point: 252° C.
1H-NMR (in DMSO-$d_6$): δ3.17 (s, 24H), 6.9–7.9 (m, 8H$_{ar.}$)

EXAMPLE 3

The procedure is as in Example 1, with the difference that instead of tetramethylammonium hydroxide solution, 36.8 g of a 40% strength aqueous tetraethylammonium hydroxide solution (0.10 mol) are used.

Yield: 43.3 g (99.4% of theory) of 2,2'-dithiodibenzoic acid mono-(tetraethylammonium) salt of the formula

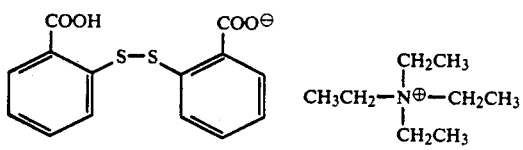

$C_{22}H_{29}NO_4S_2$ molecular weight 435.60
White powder
Melting point: 255° C.
b 1H-NMR (in DMSO-$d_6$): δ1.15 (t, 12H), 3.20 (q, 8H), 7.1–8.1 (m, 8H$_{ar.}$)

EXAMPLE 4

The procedure is as in Example 1, with the difference that instead of tetramethylammonium hydroxide solution, 73.6 g of a 40% strength aqueous tetraethylammonium hydroxide solution (0.20 mol) are used.

Yield: 56.3 g (99.7% of theory) of 2,2'-dithiodibenzoic acid di(tetraethylammonium) salt of the formula

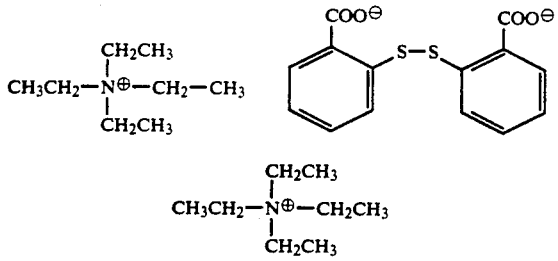

$C_{30}H_{48}N_2O_4S_2$ molecular weight 564.84
White powder
Melting point: 160° C.
1H-NMR (in DMSO-$d_6$): δ1.10 (t, 24H), 3.15 (q, 16H), 6.8–7.9 (m, 8H$_{ar.}$)

EXAMPLE 5

The procedure is as in Example 1, with the difference that instead of tetramethylammonium hydroxide solution, 101.7 g of a 20% strength aqueous tetrapropylammonium hydroxide solution (0.10 mol) are used.

Yield: 48.7 g (99.0% of theory) of 2,2'-dithiodibenzoic acid mono(tetrapropylammonium) salt of the formula

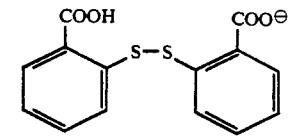

$C_{26}H_{37}NO_4S_2$ molecular weight 491.70
White powder
Melting point: 255° C.
1H-NMR (in DMSO-$d_8$): δ0.90 (t, 12H), 1.60 (m, 8H), 3.10 (m, 8H), 7.1–8.1 (m, 8H$_{ar.}$)

EXAMPLE 6

The procedure is as in Example 1, with the difference that instead of tetramethylammonium hydroxide solution, 65 g of a 40% strength aqueous tetrabutylammonium hydroxide solution (0.10 mol) are used.

Yield: 54.3 g (99.1% of theory) of 2,2'-dithiodibenzoic acid mono(tetrabutylammonium) salt of the formula

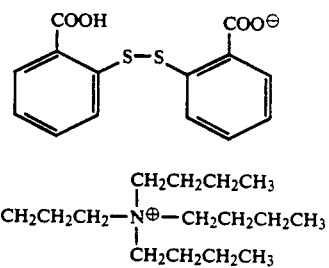

$C_{30}H_{45}NO_4S_2$ molecular weight 547.81
White powder
Melting point: 228° C.
1H-NMR (in DMSO-$d_6$): δ0.91 (t, 12H), 1.30 (m, 8H), 1.58 (m, 8H), 3.18 (m, 8H), 7.1–8.1 (m, 8H$_{ar.}$)

EXAMPLE 7

The procedure is as in Example 1, with the difference that instead of tetramethylammonium hydroxide solution, 130 g of a 40% strength aqueous tetrabutylammonium hydroxide solution (0.20 mol) are used.

Yield: 87.5 g (99.8% of theory) of 90% pure 2,2'-dithiodibenzoic acid di(tetrabutylammonium) salt of the formula

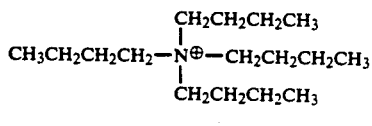

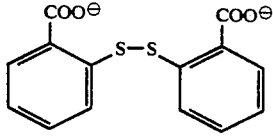

-continued

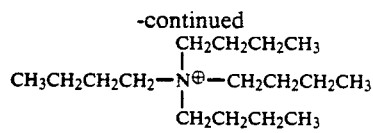

C₄₆H₈₀N₂O₄S₂ molecular weight 789.27
Viscous oil, after prolonged standing in air a waxy composition containing 10% by weight of water
Melting point: about 45° C.
1H-NMR (in DMSO-d₆): δ0.92 (t, 24H); 1.30 (m, 16H), 1.58 (m, 16H), 3.19 (m, 16H), 6.95-7.85 (m, 8H$_{ar.}$)

EXAMPLE 8

30.6 g of 2,2'-dithiodibenzoic acid (0.10 mol) are introduced into and dissolved in a solution of 8.00 g of sodium hydroxide (0.20 mol) in 800 ml of water at room temperature, while stirring. A solution of 26.6 g of tetrapropylammonium bromide (0.10 mol) in 300 ml of water is added to this solution. A solution of 3.65 g of hydrogen chloride (0.10 mol) in 100 ml of water is then slowly added dropwise, during which the product precipitates. The reaction mixture is subsequently stirred for 15 hours. The precipitate is then filtered off with suction, washed with water and dried in a through-circulation drying cabinet at 120° C.
Yield: 48.3 g (98.2% of theory) of 2,2'-dithiodibenzoic acid mono(tetrapropylammonium) salt of the formula shown in Example 5.
White powder
Melting point: 258° C.
1H-NMR (in DMSO-d₆): agrees with the spectrum of the product of Example 5.

EXAMPLE 9

The procedure is as in Example 8, with the difference that instead of tetrapropylammonium bromide, 32.2 g of tetrabutylammonium bromide (0.10 mol) are used.
Yield: 53.9 g (98.4% of theory) of 2,2'-dithiodibenzoic acid mono(tetrabutylammonium) salt of the formula shown in Example 6.
White powder
Melting point: 230° C.
1H-NMR (in DMSO-d₆): agrees with the spectrum of the product of Example 6.

EXAMPLE 10

The procedure is as in Example 8, with the difference that instead of tetrapropylammonium bromide, 33.9 g of tetrabutylphosphonium bromide (0.10 mol) are used.
Yield: 55.3 g (97.9% of theory) of 2,2'-dithiodibenzoic acid mono(tetrabutylphosphonium) salt of the formula

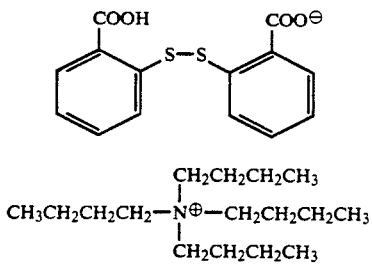

C₃₀H₄₅O₄PS₂ molecular weight 564.78
White powder

Melting point: 243° C.
1H-NMR (in DMSO-d₆): δ0.95 (t, 12H), 1.44 (m, 16H), 2.20 (m 8H), 7.15-8.05 (m, 8H$_{ar.}$)

EXAMPLE 11

The procedure is as in Example 1, with the difference that instead of tetramethylammonium hydroxide solution, 54.5 g of a 40% strength aqueous tributylmethylammonium hydroxide solution (0.10 mol) are used.
Yield: 50.3 g (99.5% of theory) of 2,2'-dithiodibenzoic acid mono(tributylmethylammonium) salt of the formula

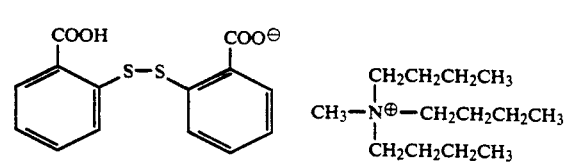

C₂₇H₃₉NO₄S₂ molecular weight 505.73
White powder
Melting point: 198° C.
1H-NMR (in DMSO-d₆): δ0.90 (t, 9h), 1.28 (m, 6H), 1.59 (m, 6H); 2.96 (s, 3H), 3,20 (m, 6H); 7.1-8.1 (m, 8H$_{ar.}$)

EXAMPLE 12

The procedure is as in Example 1, with the difference that instead of tetramethylammonium hydroxide solution, 47.7 g of a 35% strength methanolic benzyltrimethylammonium hydroxide solution (0.10 mol) are used.
Yield: 45.4 g (99.6% of theory) of 2,2'-dithiodibenzoic acid mono(benzyltrimethylammonium) salt of the formula

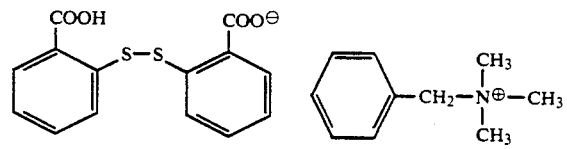

C₂₄H₂₅NO₄S₂ molecular weight 455.59
White powder
Melting point: 164° C.
1H-NMR (in DMSO-d₆): δ3.07 (s, 9H), 4.59 (s, 2H), 7.1-8.1 (m, 13H$_{ar.}$)

EXAMPLE 13

30.6 g of 2,2'-dithiodibenzoic acid (0.10 mol) are introduced into and dissolved in a solution of 8.00 g of sodium hydroxide (0.20 mol) in 350 ml of water at room temperature, while stirring. A solution of 24.5 g of barium chloride dihydrate (0.10 mol) in 70 ml of water is added to this solution. The reaction mixture is subsequently stirred at room temperature for 15 hours, during which the product precipitates. The reaction mixture is placed in a refrigerator at +4° C. for a further 24 hours and the precipitate is filtered off with suction, washed with cold water an dried in a through-circulation drying cabinet at 120° C.
Yield: 40.5 g (91.7% of theory) of 2,2'-dithiodbenzoic acid barium salt of the formula

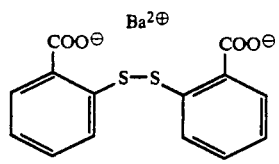

$C_{14}H_8BaO_4S_2$ molecular weight 441.67
White powder
Melting point: >330° C.
IR (KBr): ν1587, 1570, 1535, 1384, 1277, 1036, 840, 742 and 705 cm$^{-1}$

EXAMPLE 14

The procedure is as in Example 1, with the difference that instead of 2,2'-dithiodibenzoic acid, 30.6 g of 4,4'-sulphonyldibenzoic acid (0.10 mol) are used and instead of tetramethylammonium hydroxide solution, 65 g of a 40% strength aqueous tetrabutylammonium hydroxide solution (0.10 mol) are used.

Yield: 54.3 g (99.1% of theory) of 4,4'-sulphonyldibenzoic acid mono(tetrabutylammonium) salt of the formula

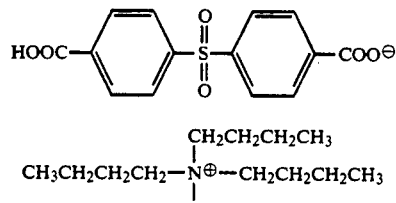

$C_{30}H_{45}NO_5S$ molecular weight 547.75
White powder
Melting point: 188° C.
1H-NMR (in DMSO-d$_6$): δ0.90 (t, 12H), 1.30 (m, 8H), 1.55 (m, 8H), 3.15 (m, 8H), 7.8–8.2 (2d, 8H$_{ar.}$)

EXAMPLE 15

30.6 g of 2,2'-dithiodibenzoic acid (0.10 mol) are suspended in 600 ml of methanol. A solution of 18.0 g of guanidine carbonate (0.10 mol) in 72 ml of water is slowly added dropwise to this suspension at about 65° C., while stirring.

After being concentrated, the reaction solution is dried in a through-circulation drying cabinet at 120° C. The product is then ground.

Yield: 42.2 g (99.5% of theory) of 2,2'-dithiodibenzoic acid di(guanidinium) salt of the formula

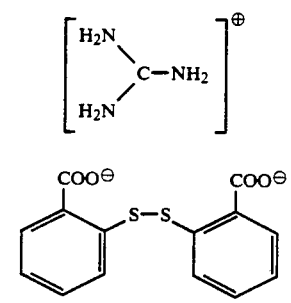

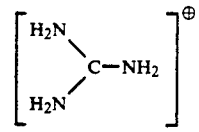

$C_{16}H_{20}N_6O_4S_2$
Molecular weight: 424.29
White powder
Melting point: 210° C.
1H-NMR (in DMSO-d$_6$): δ7.0–8.0 (m, 8H$_{ar.}$), 7.76 (s, 12H)

EXAMPLE 16

The procedure is as in Example 15, with the difference that instead of the guanidine carbonate solution, a solution of 11.5 g of 1,1,3,3-tetramethylguanidine (0.10 mol) in 35 ml of water is used.

Yield: 41.7 g (99.0% of theory) of 2,2'-dithiodibenzoic acid mono(1,1,3,3-tetramethylguanidinium) salt of the formula

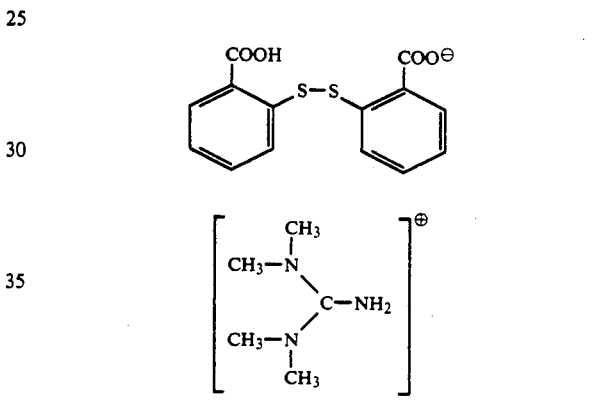

$C_{19}H_{23}N_3O_4S_2$ molecular weight: 421.53
White powder
Melting point: 205° C.
1H-NMR (in DMSO-d$_6$): δ2.9 (s, 12H), 7.1–8.0 (m, 8H$_{ar.}$), 8.1 (s, 2H)

EXAMPLE 17

47 g of sodium hydroxide are dissolved in 750 ml of water. 180 g of industrial 2,2'-dithiodibenzoic acid with a purity of 85% of by weight are stirred into and dissolved in the cooled sodium hydroxide solution. The solution is filtered off from dirt particles. 296 g of 45% strength aqueous tetrapropylammonium bromide solution are added to the filtrate. Gaseous carbon dioxide is then passed in, while stirring, until the pH is 7.5. The mixture is subsequently stirred for one hour and the solid is then filtered off with suction through a suction filter. The product is washed with 3000 ml of water, sucked thoroughly dry and dried for 24 hours at 100° C. in vacuo.

Yield: 222 g (90% of theory) of 2,2'-dithiodibenzoic acid mono(tetrapropylammonium) salt.

$C_{26}H_{37}NO_4S_2$ molecular weight 491.70
Melting point: 250° C.
1H-NMR (in DMSO-d$_6$): δ0.9 (t, 12H), 1.6 (m, 8H), 3.1 (m, 8H), 7.1–8.1 (m, 8 H$_{ar.}$)

EXAMPLE 18

The procedure is as in Example 17, with the difference that instead of the tetrapropylammonium bromide solution, 377 g of 45% strength aqueous tetrabutylphosphonium bromide solution are added and carbon dioxide is passed in until the pH is 7.0.

Yield: 277.5 g (98.4% of theory)

2,2'-Dithiodibenzoic acid mono(tetrabutylphosphonium) salt.

$C_{30}H_{45}O_4PS_2$ molecular weight 564.78

Melting point: 237° C.

1H-NMR (in DMSO-d$_6$): δ0.95 (t, 12H), 1.45 (m, 16H), 2.2 (m, 8H), 7.1–8.1 (m, 8H$_{ar}$).

We claim:

1. A compound of the formula I

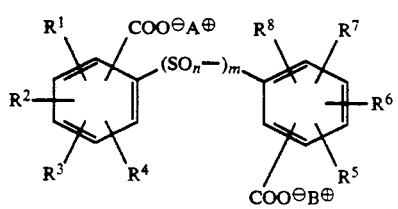

wherein n denotes 0, 1 or 2 is m denotes 1, and n denotes 0 if m denotes 2 or 3, A⊕ and B⊕ independently of one another denote a proton, with the limitation that they do not both simultaneously denote protons, or an ion of the formula II

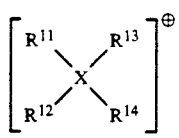

or an ion of the formula III

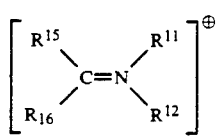

wherein X represents nitrogen, phosphorus, arsenic or antimony; $R^{11}$, $R^{12}$, $R^{13}$ and $R^{14}$ independently of one another represent hydrogen, with the limitation that they do not all simultaneously represent hydrogen; ($C_1$–$C_{10}$)-alkyl; oxyethyl of the formula —(CH$_2$—CH$_2$—O)$_p$—R$^9$, wherein R$^9$ is hydrogen, ($C_1$–$C_4$)alkoxy or acyl and p is a number from 1 to 10; ($C_5$–$C_{12}$)-cycloalkyl; ($C_6$–$C_{12}$)-aryl or $C_6$–$C_{12}$-aryl-($C_1$–$C_6$)-alkyl and are optionally substituted by hydroxyl, ($C_1$–$C_4$)-alkoxy, primary, secondary or tertiary amino groups, acid amide groups, fluorine, chlorine or bromine; $R^{15}$ and $R^{16}$ independently of one another represent hydrogen, ($C_1$–$C_6$)alkyl or amino or the formula IV

wherein $R^{17}$ and $R^{18}$ independently of one another denote hydrogen or ($C_1$–$C_6$)-alkyl; and it being possible for the radicals $R^{11}$ and $R^{13}$ or $R^{11}$ and $R^{15}$ independently of one another to form together a 5- to 12-membered ring system which is optionally substituted or contains further hetero atoms; $R^1$ to $R^8$ independently of one another denote hydrogen, ($C_1$–$C_{30}$)-alkyl; ($C_2$–$C_{30}$)-alkenyl; ($C_2$–$C_{30}$)-alkynyl, ($C_1$–$C_4$)-alkoxy; a group of the formula -((C$_2$–C$_5$)-alkylene-o)$_q$-R$^{10}$, wherein R$^{10}$ is hydrogen, ($C_1$–$C_4$)alkyl or acyl and q is a number from 1 to 10; ($C_5$–$C_{12}$)-cyclalkyl; ($C_6$–$C_{12}$)-aryl; ($C_6$–$C_{12}$)-aryl-($C_1$–$C_6$)-alkyl, fluorine, chlorine, bromine, iodine, nitro, cyano hydroxyl, a sulphone group, a sulphonic acid group, a carboxylic acid ester group or a group —NR$^{21}$R$^{22}$, wherein R$^{21}$ and R$^{22}$ independently of one another are hydrogen or ($C_1$–CH$_4$)-alkyl, the aliphatic, cycloaliphatic, araliphatic and aromatic radicals being optionally substituted by the carboxylic acid group or salts or amides or esters thereof; the sulphonic acid group or salts or amides or esters thereof; hydroxyl; ($C_1$–$C_4$)-alkyl; ($C_1$–$C_4$)-alkoxy; primary, secondary or tertiary amino groups, fluorine, chlorine or bromine, or one or more hetero atoms, and optionally in each case two of the radicals $R^1$ to $R^4$ or $R^5$ to $R^8$ independently or one another together form a 5- to 12-membered ring system which is optionally substituted or contains one or more hetero atoms.

2. Compound according to claim 1, characterised in that, in the formula I, the substituents COO⁻A⁺ and COO⁻B⁺ are in the 2,2'- or in the 4,4'-position.

3. Compound according to claim 1, characterised in that, in the formula I, m denotes 2 and n denotes 0, and the substituents COO⁻A⁺ and COO⁻B⁺ are in the 2,2'-position.

4. Compound according to claim 1, characterised in that it has the formula Ia

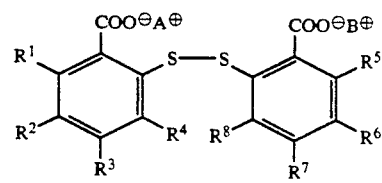

wherein $R^1$, $R^3$, $R^5$ and $R^7$ denote hydrogen, $R^2$, $R^4$, $R^6$ and $R^8$ denote hydrogen or chlorine and A⊕ and B⊕ have one of the meanings given in claim 1.

5. Compound according to claim 1, characterised in that it has the formula Ib

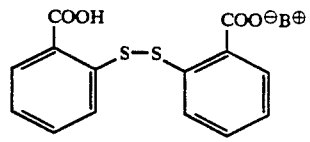

wherein B⊕ denotes tetramethylammonium, tetraethylammonium, tetrapropylammonium, tetrabutylammonium, tetrapentylammonium, tetrahexylammonium, tetraheptylammonium, tetraocytlammonium, tetranonylammonium, tetrakis-(decyl)-ammonium, tetradodecylammonium, tributylmethylammonium, benzyltrimethylammonium, ethylhexadecyldimethylammonium, benzyldimethylhexadecylammonium, benzyltriethylammonium, hexadecyltrimethylammonium, phenyltrimethylammonium, hexadecylpyridinium, guanidinium, 1,1,3,3-tetramethylguanidinium, tetrapropylphosphonium, tetrabutylphosphonium, tetrapentylphosphonium, benzyltriphenylphosphonium or hexadecyltributylphosphonium.

6. Compound according to claim 1, characterised in that it has the formula Ic

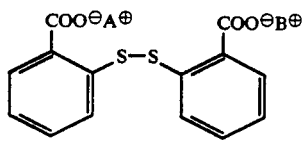

(Ic)

wherein $A^{\oplus}$ and $B^{\oplus}$ are identical and denote tetramethylammonium, tetraethylammonium, tetrapropylammonium, tetrabutylammonium, tetrapentylammonium, tetrahexylammonium, tetraheptylammonium, tetraocytlammonium, tetranonylammonium, tetrakis(decyl)ammonium, tetradodecylammonium, tributylmethylammonium, benzyltrimethylammonium, ethylhexadecyldimethylammonium, benzyldimethylhexadecylammonium, benzyltriethylammonium, hexadecyltrimethylammonium, phenyltrimethylammonium, hexadecylpyridinium, guanidinium, 1,1,3,3-tetramethylguanidinium, tetrapropylphosphonium, tetrabutylphosphonium, tetrapentylphosphonium, benzyltriphenylphosphonium or hexadecyltributylphosphonium.

7. Compound according to claim 1, characterised in that it has the formula Ie

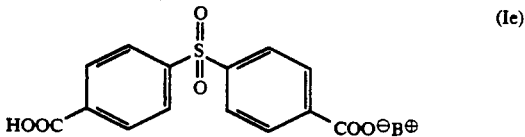

(Ie)

wherein $B^{\oplus}$ denotes tetramethylammonium, tetraethylammonium, tetrapropylammonium, tetrabutylammonium, tetrapentylammonium, tetrahexylammonium, tetraheptylammonium, tetraoctylammonium, tetrapropylphosphonium or tetrabutylphosphonium.

* * * * *

UNITED STATES PATENT AND TRADEMARK OFFICE
CERTIFICATE OF CORRECTION

PATENT NO. : 5,274,184
DATED : December 28, 1993
INVENTOR(S) : NAGL et al

It is certified that error appears in the above-indentified patent and that said Letters Patent is hereby corrected as shown below:

Col. 1, line 24, "equivalent proton" should read: --equivalent portion--.

Col. 4, line 35, "di-(tetrapropylammonium)" should read:--mono-(tetrabutylammonium)--.

Col. 14, line 41, "$B^{\oplus}Y_b^{\oplus}$" should read: -- $B^{\oplus}Y_b^{\ominus}$ --.

Col. 14, line 47, "$Y_b^{\oplus}$" should read: -- $Y_b^{\ominus}$ -

Col. 14, line 57, "$E^{\oplus}$ and $E^{\oplus}$" should read: -- $E^{\oplus}$ and $F^{\oplus}$ --.

Col. 15, line 16, "$B^{\oplus}Y_b^{\oplus}$" should read: -- $B^{\oplus}Y_b^{\ominus}$ --.

Col. 15, line 32, "$Y_b^{\oplus}$" should read: -- $Y_b^{\ominus}$ --.

Col. 15, lines 34-35 "according to the inventional ready precipitates out an addition" should read: -- according to the invention already precipitates out on addition --.

Col. 15, line 56, "$Y_b^{\oplus}$" should read: -- $Y_b^{\ominus}$ --.

Col. 15, line 68, "of the general formula if" should read: -- of the general formula If --.

UNITED STATES PATENT AND TRADEMARK OFFICE
CERTIFICATE OF CORRECTION

PATENT NO. : 5,274,184
DATED : December 28, 1993
INVENTOR(S) : NAGL ET AL

It is certified that error appears in the above-indentified patent and that said Letters Patent is hereby corrected as shown below:

Col. 16, line 20 "$B^{\ominus}$" should read: -- $B^{\oplus}$ --.

Col. 16, line 29 in the formula (Va) the carboxyl substituent on the left-hand aryl ring should appear as: --$COO^{\ominus}E^{\oplus}$ --.

Col. 16, line 39 "compound $A^{\oplus}Y_b^{\ominus}$," should read: -- compound $A^{\oplus}Y_a^{\ominus}$ or $B^{\oplus}Y_b^{\ominus}$, --

Col. 16, line 41 "$Y_a^{\oplus}$ and $Y_b^{\oplus}$" should read: --$Y_a^{\ominus}$ and $Y_b^{\ominus}$ --.

Col. 16, line 47 "$R^{11}$ and to $R^{14}$" should read: -- $R^{11}$ to $R^{14}$ --.

Col. 17, line 53 in formula (V) the carboxyl substituent on the left-hand aryl ring should appear as: -- $COO^{\ominus}E^{\oplus}$ --.

Col. 20, line 16, "(in DMSO-$d_8$)" should read: -- (in DMSO-$d_6$) --.

Col. 21, lines 61-65, the central atom in the formula for the tetrabutylphosphonium ion should be P, not N.

UNITED STATES PATENT AND TRADEMARK OFFICE
CERTIFICATE OF CORRECTION

PATENT NO. : 5,274,184
DATED : December 28, 1993
INVENTOR(S) : NAGL ET AL

It is certified that error appears in the above-indentified patent and that said Letters Patent is hereby corrected as shown below:

Col. 23, line 38 "$C_{30}H_{45}NO_5S$" should read: -- $C_{30}H_{45}NO_6S$ --.

Col. 24, line 41 "$C_{19}H_{23}H_3O_4S_2$" should read: -- $C_{19}H_{23}N_3O_4S_2$ --.

Col. 24, line 51 "85% of by weight" should read: -- 85% by weight --.

Col. 25, line 28 "is m denotes 1," should read: -- if m denotes 1, --.

Signed and Sealed this

Sixth Day of September, 1994

Attest:

BRUCE LEHMAN

Attesting Officer     Commissioner of Patents and Trademarks